United States Patent [19]

Bolesky

[11] Patent Number: 4,822,366
[45] Date of Patent: Apr. 18, 1989

[54] MODULAR KNEE PROSTHESIS

[75] Inventor: Richard C. Bolesky, Warsaw, Ind.

[73] Assignee: Boehringer Mannheim Corporation, Indianapolis, Ind.

[21] Appl. No.: 919,365

[22] Filed: Oct. 16, 1986

[51] Int. Cl.[4] .............................................. A61F 2/38
[52] U.S. Cl. ..................................................... 623/20
[58] Field of Search ............................. 623/20, 18, 22

[56] References Cited

U.S. PATENT DOCUMENTS

| | | |
|---|---|---|
| 4,016,606 | 4/1977 | Murray et al. . |
| 4,209,861 | 7/1980 | Walker et al. . |
| 4,219,893 | 9/1980 | Noiles . |
| 4,224,696 | 9/1980 | Murray et al. . |
| 4,257,129 | 3/1981 | Volz . |
| 4,301,553 | 11/1981 | Noiles . |
| 4,309,778 | 1/1982 | Buechel et al. . |
| 4,340,978 | 7/1982 | Buechel et al. . |
| 4,358,859 | 11/1982 | Schurman ............................ 623/20 |
| 4,404,691 | 9/1983 | Buning et al. . |
| 4,462,120 | 7/1984 | Rambert et al. . |
| 4,470,158 | 9/1984 | Pappas et al. . |
| 4,578,081 | 3/1986 | Harder ................................. 623/22 |
| 4,586,933 | 5/1986 | Shoji .................................... 623/20 |
| 4,634,444 | 6/1987 | Noiles .................................. 623/20 |
| 4,662,889 | 5/1987 | Zichner et al. . |
| 4,673,408 | 6/1987 | Grobbelaar .......................... 623/20 |
| 4,676,797 | 6/1987 | Anapliotis ........................... 623/18 |

Primary Examiner—Richard J. Apley
Assistant Examiner—James Prizant
Attorney, Agent, or Firm—Barnes & Thornburg

[57] ABSTRACT

A modular knee prosthesis assembly for the replacement of a portion of the knee joint is provided. The assembly has a femoral component that is formed to include first bearing surfaces and first means for demountably receiving an optional femoral stem member. The assembly also has a tibial component that is formed to include a platform and second means for demountably receiving an optional tibial stem member. The assembly includes a separate tibial insert that is configured to be supported by the tibial component platform. The tibial insert is formed to include second bearing surfaces that are configured to mate with the first surfaces on the femoral component to permit pivotal movement between the femoral component and the tibial component.

14 Claims, 3 Drawing Sheets

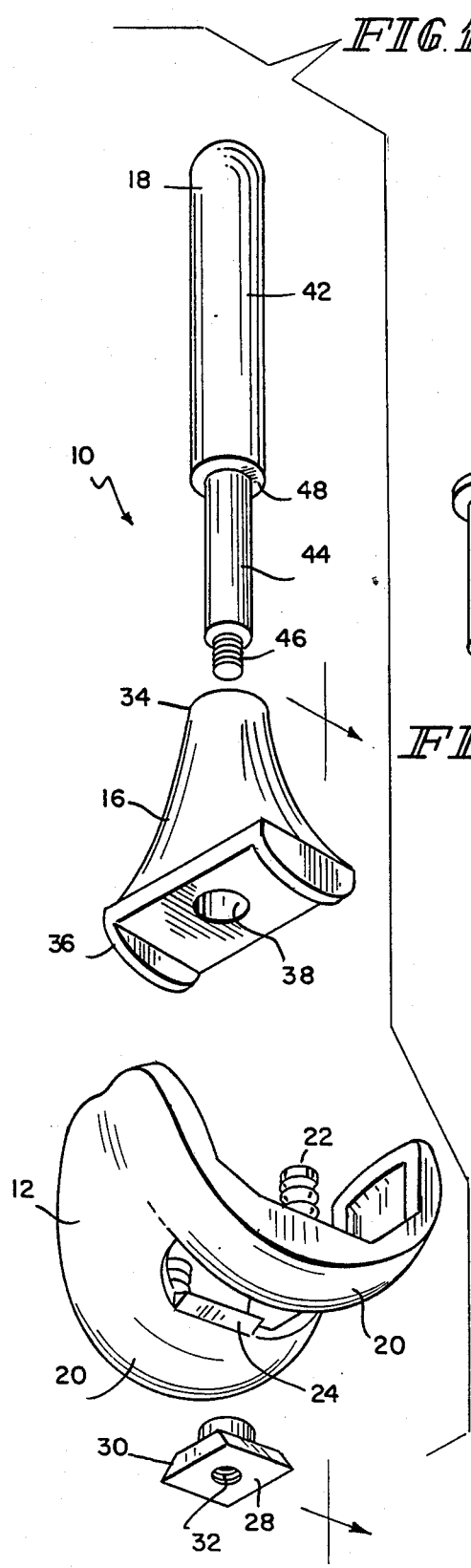
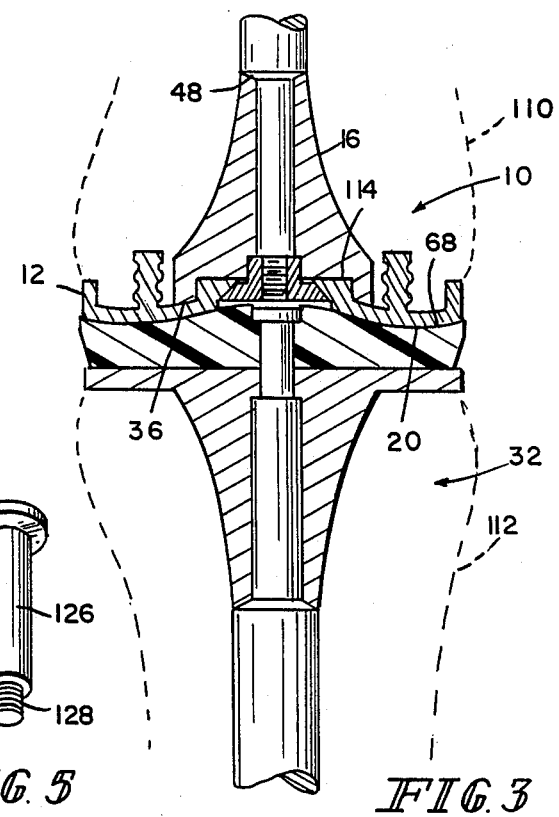
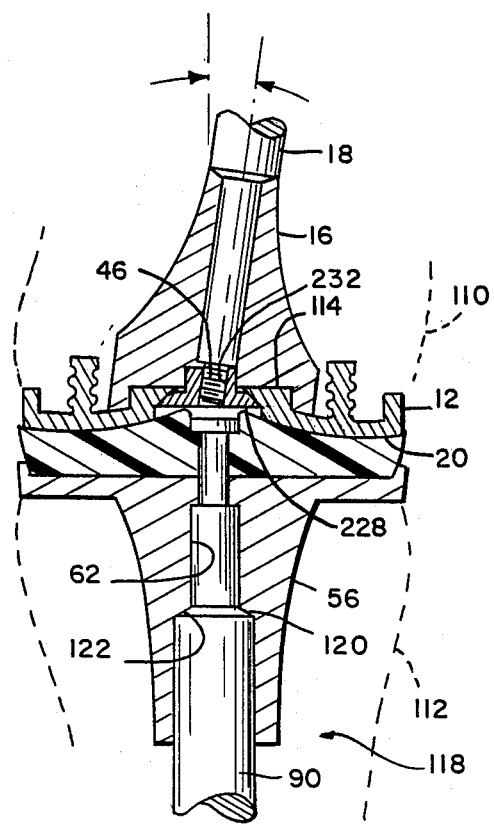

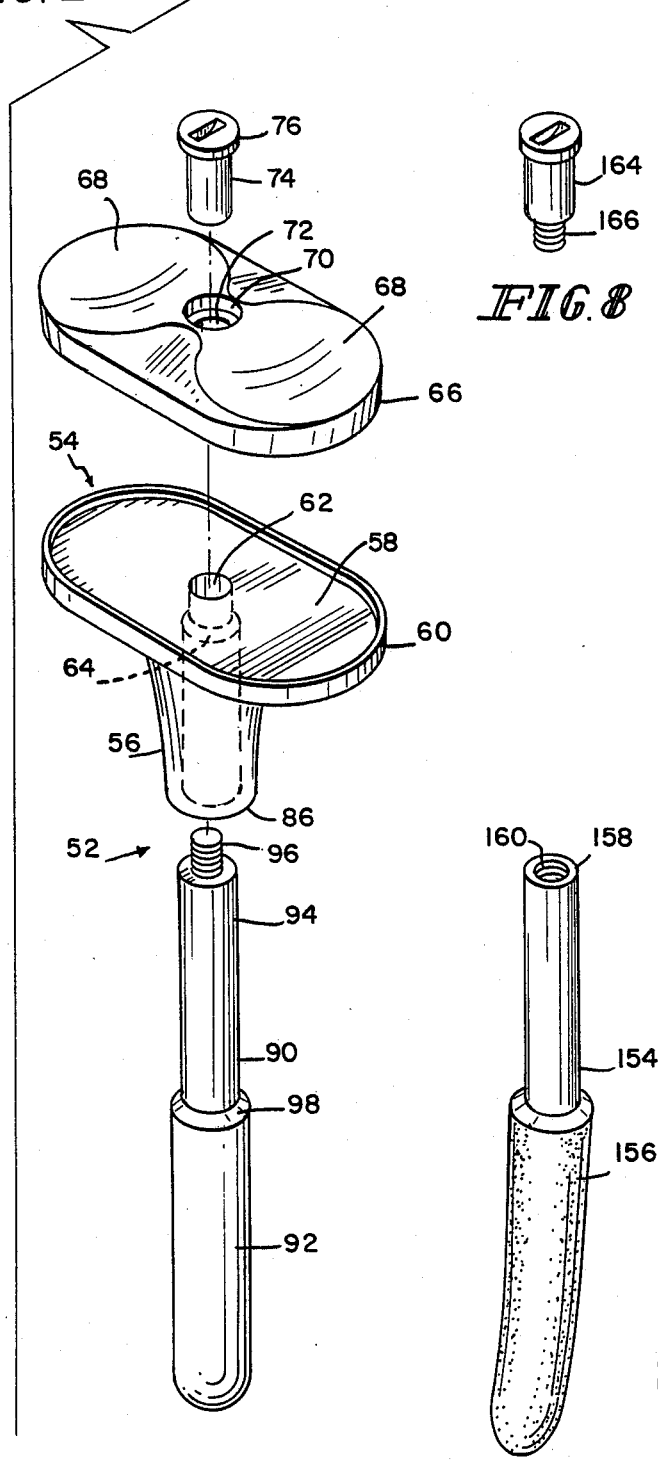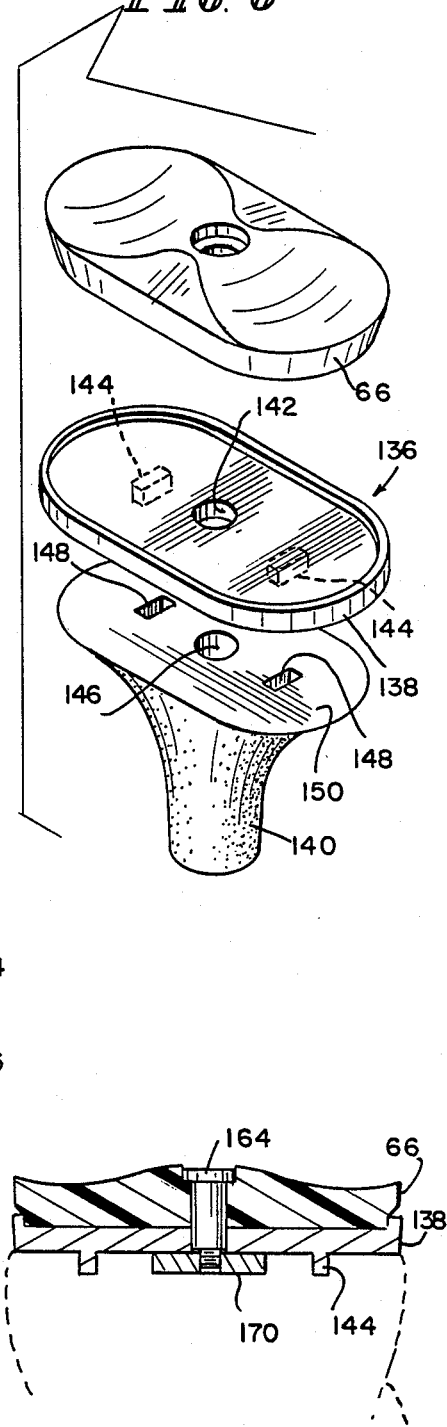

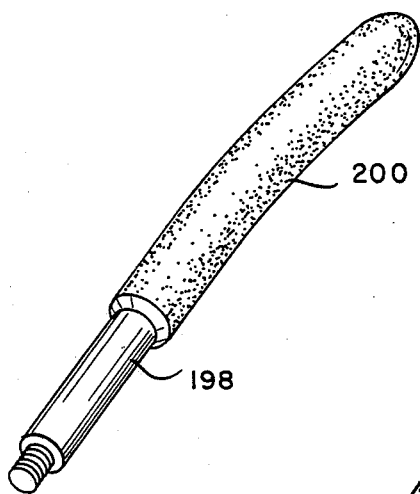
FIG. 12
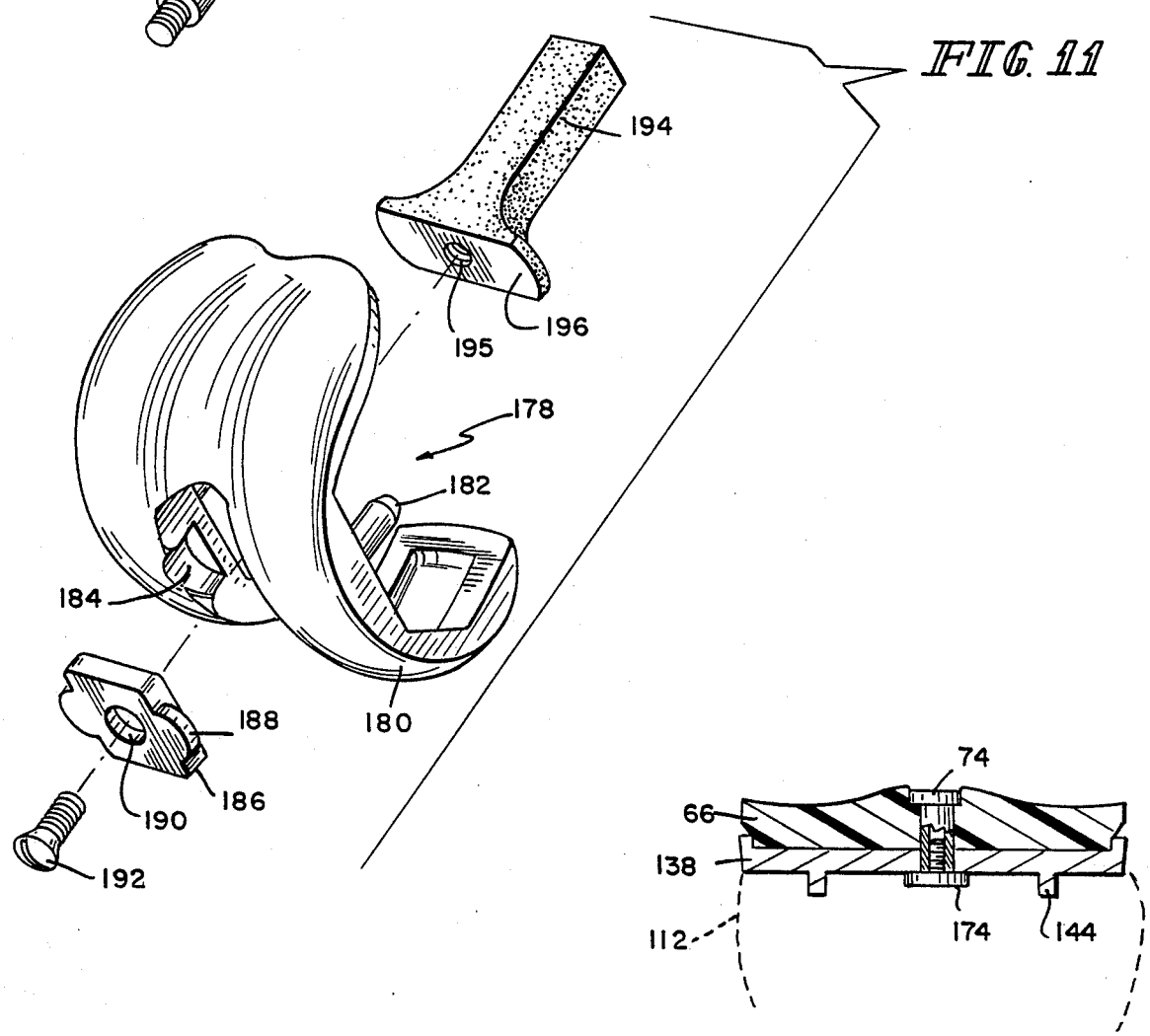
FIG. 11
FIG. 10

MODULAR KNEE PROSTHESIS

BACKGROUND AND SUMMARY OF THE INVENTION

The present invention relates to prostheses for replacement of a portion of the knee joint. More particularly, the present invention relates to a modular prosthesis for replacement of the distal portion of the femur and the proximal portion of the tibia.

Present prostheses for the replacement of the knee joint generally include two structures. The conventional prosthesis generally includes a femoral portion that is designed to replace the distal portion of the natural femur. The femoral portion may be formed with or without an elongated stem that is designed to extend into the shaft of the femur. The conventional knee prosthesis also generally includes a tibial portion that is designed to replace the proximal portion of the tibia. Like the femoral portion, the tibial portion may be formed with or without an elongated stem that is designed to extend into the shaft of the tibia. The tibial portion normally has a bearing surface or is provided with a separate bearing element to mate with bearing surfaces on the femoral portion to permit movement between the femur and the tibia. For a discussion of the structure and use of conventional knee prostheses, reference is made to U.S. Pat. Nos. 4,470,158, 4,340,978, 4,309,778, 4,301,553, and 4,219,893.

Because conventional knee prostheses are generally provided as two devices, the practice has been to maintain a large inventory of prostheses of different sizes and configurations, both with and without elongated stems, to accommodate the different bone sizes that are to be replaced. Generally, the patient is evaluated using conventional x-ray procedures, or some other means, to determine the approximate bone size, and consequently the approximate required prosthesis size. During the replacement operation, several different prostheses are made available as suggested by the x-ray evaluation. The appropriate prosthesis is then selected for insertion into the patient at the time of the replacement operation.

One problem with the conventional knee prosthesis is that the hospital has to maintain a large number of differently sized and oriented prostheses to accommodate different sizes of bones to be replaced. Generally, a supply of prostheses with and without elongated stems must be maintained in the inventory. Also, the prostheses with different shapes and angles of the stem must be maintained. Even with this large inventory of prostheses, it is often difficult to have a prosthesis available that is sized and shaped exactly for the individual patient.

Prostheses having femoral portions and tibial portions with removable stems are known. One such prosthesis is shown in U.S. Pat. No. 4,462,120. U.S. Pat. No. 4,462,120 discloses a knee prosthesis having upper and lower members that are provided with externally threaded, tapered shanks that are detachably secured to each member. The threaded shanks are disclosed to be uniformly sized, and are shown in only one orientation, with the axis of the shank generally perpendicular to a transverse plane passing through the planar surfaces of the upper and lower members. Neither the upper member nor the lower member is configured to be implanted without the threaded shank. Also, only one size and shape of threaded shank is disclosed for use with either the upper member or the lower member. This prosthesis is thus limited in flexibility because of the necessity for inclusion of the shanks, and because the shanks are limited in structure and design.

Prostheses having limited interchangeable components of different sizes are disclosed in U.S. Pat. Nos. 4,257,129 and 4,404,691. U.S. Pat. No. 4,257,129 discloses a prosthetic tibial implant having a replaceable articulation member removably attached to an anchor member. The patent discloses that different sizes of articulation members are available and interchangeable with each other. The articulation member is secured to the anchor member by the use of a vertical pin that is secured by a clip. The patent does not disclose that the anchor member can be utilized without a stem. In fact, the stem must be a part of the anchoring member in order to receive the vertical pin to lock the articulation member in place. This prosthesis is limited in flexibility because of the requirement to utilize the anchor member with the stem.

U.S. Pat. No. 4,404,691 discloses a knee prosthesis in which different sizes of femoral components are interchangeable with different sizes of tibial components. The femoral components and the tibial components are each unitary structures, with only their sizes being different. Neither the femoral components, nor the tibial components have stems that are removable. Although the patent does disclose some degree of modularity, the flexibility is limited to different sizes of components being interchangeable with each other. The patent does not disclose that any of the femoral components or tibial components can be used without a stem attached.

One object of the present invention is to provide a modular knee prosthesis that offers a great deal of flexibility in its assembly, both as to the size and shape of the assembled device.

Another object of the present invention is to provide a modular knee prosthesis that may be assembled in the operating room before any component of the prosthesis is inserted into the patient.

Yet another object of the present invention is to provide a modular knee prosthesis in which the femoral component and the tibial component are designed to function with or without an optional stem.

Yet another object of the present invention is to provide a modular knee prosthesis that may include a stem portion that is shaped to fit a curvature within the bone structure, if necessary.

According to the present invention, a modular knee prosthesis assembly for replacement of a portion of the knee joint is provided. The assembly comprises a femoral component that is formed to include first bearing surfaces and first means for demountably attaching an optional femoral stem member. The assembly also comprises a tibial component that is formed to include a platform and second means for demountably attaching an optional tibial stem member. The assembly also includes a separate tibial insert that is configured to be supported by the tibial component platform. The tibial insert is formed to include second bearing surfaces that are configured to mate with the first surfaces on the femoral component to permit pivotal movement between the femoral component and the tibial component.

One feature of the present invention is that the femoral component and the tibial component are designed to function either with or with-out an optional stem member. One advantage of this feature is that the same tibial or femoral component can be utilized in more than one application.

In preferred embodiments of the present invention, the femoral component is selected from a group consisting of differently sized and shaped femoral components, with the group of femoral components having the first attaching means generally uniformly sized. One feature of the foregoing structure is that a number of femoral components are available, with the selection of the femoral component dictated by the needs of the patient. Each femoral component of the group has a first attaching means that is generally uniformly sized with the other components of the group. One advantage of this feature is that each femoral component in the group is interchangeably engageable with an optional femoral stem member to increase the flexibility of the assembly.

Also in preferred embodiments of the present invention, the tibial component is selected from a group consisting of differently sized tibial components, with the group of tibial components having the second attaching means generally uniformly sized. One feature of the foregoing structure is that differently sized and shaped tibial components are available, with the selection depending upon the requirements of the patient. Each tibial component in the group has second attaching means that are generally uniformly sized. One advantage of this feature is that each tibial component in the group is interchangeably engageable with an optional tibial stem member to increase the flexibility of the assembly.

Also in preferred embodiments of the present invention, the assembly includes at least one femoral stem extension that has a lower portion that is configured to be attached to the femoral stem member to increase the length of the stem attached to the femoral component. The femoral stem extension is selected from a group consisting of differently sized and shaped femoral stem extensions, with the group of femoral stem extensions having the lower portions generally uniformly sized. One feature of the foregoing structure is that the differently sized and shaped femoral stem extensions have lower portions for mating with the femoral stem members that are uniformly sized. One advantage of this feature is that any of the group of femoral stem extensions is optionally mateable with any of the femoral stem members to increase the flexibility of the assembly.

The modular knee prosthesis of the present invention thus provides the ability to assemble a custom knee prosthesis by selecting different sizes and shapes of individual components to meet the requirements of the individual patient more precisely. The interchangeability of the components of the prosthesis greatly reduces the inventory required to be maintained by the hospital Also, the interchangeability of the components greatly increases the flexibility of the system, and provides for the assembly of a knee prosthesis that may otherwise be unavailable.

Additional objects, features, and advantages of the invention will be apparent to those skilled in the art upon consideration of the following detailed description of preferred embodiments exemplifying the best mode of carrying out the invention as presently perceived.

BRIEF DESCRIPTION OF THE DRAWINGS

The detailed description particularly refers to the accompanying figures in which:

FIG. 1 is an exploded perspective view of one embodiment of a femoral portion of the modular knee prosthesis of the present invention showing a femoral component, a femoral stem member, and a femoral stem extension;

FIG. 2 is an exploded perspective view of one embodiment of a tibia portion of the present invention showing a tibial component, a tibial stem member, a tibial stem extension, and a tibial insert;

FIG. 3 is a transverse sectional view through the femur and tibia showing one embodiment of the modular knee prosthesis of the present invention in place;

FIG. 4 is a view similar to FIG. 3 showing another embodiment of the present invention in which the femoral stem member is angled somewhat with respect to a vertical axis of the knee prosthesis;

FIG. 5 is a perspective view of a bolt that is utilized to attach the femoral stem member to the femoral component when the femoral stem extension is not utilized;

FIG. 6 shows a modification of the tibial portion shown in FIG. 5 with the tibial component and the tibial stem member being separate elements;

FIG. 7 is a perspective view showing a modified tibial stem extension that may be utilized with the tibial portions shown in FIGS. 5 and 6;

FIG. 8 shows a modified bolt that may be used to mate with the modified stem shown in FIG. 7;

FIG. 9 is a transverse sectional view through the tibia showing the embodiment of FIG. 6 in place without the tibial stem member;

FIG. 10 is a view similar to FIG. 9 showing a modified tibial portion;

FIG. 11 is an exploded perspective view showing a modified femoral component as well as a modified femoral stem member; and FIG. 12 is a perspective view showing a modified femoral stem extension that may be used with the embodiment shown in FIG. 1.

DETAILED DESCRIPTION OF THE DRAWINGS

Referring now to the drawings, FIG. 1 shows one embodiment of a femoral portion 10 that is adapted to replace the distal portion of the femur, including replacement of the lateral and medial condyle. FIG. 2 shows one embodiment of a tibial portion 52 that is adapted to replace the proximal portion of the tibia, including replacement of the tibial lateral and medial condyles. Both the femoral portion 10 and the distal portion 52 are assembled using separate, individually sized components. Each component is typically selected from a group of components of various sizes and shapes to form the replacement portion that will exactly fit the patient. Thus, both the femoral portion 10 and the tibial portion 52 are modularized in the sense that each portion is assembled using selectively sized components that are interchangeable with each other.

FIG. 1 shows the femoral portion 10 broken down into its individual components. The femoral portion 10 includes a femoral or first component 12 that is adapted to replace the extreme distal portion of the femur (FIG. 3). The femoral portion 10 also includes a femoral stem or second component 16 that is adapted to mate with the femoral component 12 and to extend into a cavity formed in the femur. The femoral portion 10 further includes a femoral stem extension or third component 18 that is adapted to mate with the femoral stem 16 and femoral component 12 to form a completed femoral portion 10. The femoral stem extension 18 is adapted to extend further into a cavity in the femur beyond the femoral stem 16. The femoral component 12 includes on its obverse surface two condyles or articulating surfaces 20 that are configured to replace the condyles of the distal portion of the femur. Two upwardly extending posts 22 are attached to the reverse of the femoral component 12 that are configured to extend into the distal portion of the femur to secure the femoral component 12 somewhat to the femur. The posts 22 permit the femoral component 12 to be used without either the femoral stem 16 or the femoral stem extension 18 if desired. An angled ledge 24 is formed between the articulating surfaces 20, and configured to receive and support a nut fastener 28. The nut 28 includes angled faces 30 that mate with the ledges 24 to position and hold the nut 28 in place. A threaded bore 32 is formed through the nut 28.

The femoral stem 16 has a proximal end 34 and a distal end 36. The distal end 36 is configured to mate with the femoral component 12 as best shown in FIG. 3. An axial bore 38 is formed through the femoral stem 16 and is adapted to receive a portion of the femoral stem extension 18. The femoral stem extension 18 includes a proximal portion 42 and a reduced diameter distal portion 44. The distal portion 44 terminates in a threaded end 46. The demarcation between the proximal portion 42 and the distal portion 44 is marked by a chamfer 48 that is configured to abut the proximal end 34 of the femoral stem 16.

The femoral portion 10 shown in FIG. 1 is assembled by inserting the distal portion 44 of the femoral stem extension 18 through the bore 38 in the femoral stem 16. The distal end 36 of the femoral stem is then mated with the femoral component 12 and the threaded end 46 of the femoral stem extension 18 is engaged with the threaded bore 32 of the nut 28 to secure the components together to form an assembled femoral portion 10. This assembly is shown broken away in FIG. 3.

The femoral stem 16 and the proximal portion 42 of the femoral stem extension 18 may have any of several surface treatments, including, but not limited to, blasted, smooth, porous bony-ingrowth, and coated. In addition, each of the components forming the femoral portion 10 may be selected from a group of components having slightly different shapes and sizes to conform to the requirements of the individual patient. For example, the femoral stem extension 18 is selected from a group of femoral stem extensions that are differently sized and shaped, with each of the femoral stem extensions in the group being interchangeable to provide the modular concept. The femoral stem 16 and stem extension 18 may be formed from different, but compatible, materials to achieve varying modes of rigidity.

FIG. 2 shows a tibial portion 52 that is adapted to replace the proximal portion of the tibia (FIG. 3). The tibial portion 52 includes a tray-like tibial component 54. A tibial stem 56 is-formed as a part of the tibial component 54 in this-.-embodiment. The tibial component 54 is formed to include a generally planar support surface 58 that is oriented substantially perpendicular to a generally longitudinal axis of the tibia. The support surface 58 is bounded by an upwardly and peripherally extending rim 60. A bore 62 is formed through the tibial component 54 and attached tibial stem 56. The bore 62 is formed to include a ledge 64 (shown only in dotted) that is positioned somewhat below the tibial component 54.

A tibial insert 66 is provided to be received in the tibial component 54 to replace the extreme proximal portion of the tibia. The tibial insert 66 is formed to include two slightly concave bearing surfaces 68 that are designed to replace the medial and lateral condyles of the tibia. The bearing surfaces 68 of the tibial insert 66 are adapted to support and mate with the articulating surfaces 20 on the femoral component 12. The shape and configuration of the articulating surfaces 20 and the bearing surfaces 68 permit flexing movement between the femoral portion 10 and the tibial portion 52 to simulate somewhat the movements of a natural knee joint. Illustratively, the tibial insert 66 is formed from a high molecular weight polyethylene material. It will be understood that the tibial insert 66 may be formed from other suitable polymeric or composite materials, for example polytetrafluorethylene-type materials. The tibial insert 66 includes a bore 70 having an upwardly facing ledge 72. A nut 74 is provided that includes a shoulder 76 that cooperates with the ledge 72 to position the nut 74 within the bore 70 in the tibial insert 66.

A tibial stem extension 90 is provided for the tibial portion 52 that is adapted to extend into a cavity in the tibia. The tibial stem extension 90 includes a distal portion 92 and a slightly reduced diameter proximal portion 94. The proximal portion 94 terminates proximally in a threaded end 96. The demarcation between the reduced diameter proximal portion 94 and the distal portion 92 is marked by a chamfer 98 that is configured to mate with the distal end 86 of the tibial stem 56. The distal portion 92 of the tibial stem extension 90, like the femoral stem extension 18, may have any of several surface treatments, including, but not limited to, blasted, smooth, porous bony-ingrowth, and coated. The tibial portion 52 and stem extension 90 may be formed from different, but compatible, materials to achieve varying modes of rigidity.

To assemble the tibial portion 52 illustrated in FIG. 2, the tibial stem extension 90, and specifically the proximal portion 94, is inserted into the bore 62 in the tibial stem 56 and tibial component 54. The tibial insert 66 is then placed on the support surface 58 within the rim 60. The rim 60 acts to retain the tibial insert 66 and to prevent rotation of the tibial insert 66 on the support surface 58. It will be understood that the rim 60 may be omitted in any of the embodiments illustrated if rotation of the tibial insert 66 with respect to the tibial component 54 is desired. The nut 74 is then inserted into the bore 70 in the tibial insert 66 to engage the threaded end 96 of the tibial stem extension 90. Tightening the nut 74 secures the individual components to form the assembled tibial portion 52. It will be understood that each of the individual components of the tibial portion 52 is selected from a group of components having different sizes and shapes to conform to the requirements of the patient. Each component within each group is interchangeable to provide the modular concept.

FIG. 3 shows an assembled femoral portion 10 illustrated in FIG. 1 and an assembled tibial portion 52 shown in FIG. 2 in place within a femur 110 and a tibia 112, respectively. It will be understood that the assembled femoral portion 10 and the assembled tibial portion 52 have been inserted into the femur 110 and tibia 112 in a conventional manner. FIG. 3 illustrates the cooperation between the slightly convex articulating surfaces 20 and the slightly concave bearing surfaces 68 to permit the femoral portion 10 to be supported upon the tibial portion 52 to allow for flexing movement. FIG. 3 also illustrates the mating of the femoral stem 16 to the femoral component 12. The femoral component 12 is formed to include a platform 114 that engages the distal end 36 of the femoral stem 16 to position the femoral stem 16 with respect to the femoral component 12.

FIG. 4 illustrates another embodiment of the present invention in which the femoral stem 16 has been oriented somewhat differently to permit a different configuration between the femoral stem 16 and the femoral component 12. The femoral stem 16 has been angled somewhat with respect to an axis that is generally perpendicular to the plane of the articulating surfaces 20. Angling the femoral stem 16 allows the femoral stem 16 to assume an angle different than that shown in FIG. 3. An angled femoral stem 16 may be advantageous to accommodate a femur that is somewhat angled, and particularly to be inserted into either a left or right femur because of possible differences between the left and the right femur. A modified nut 228 is provided having an angled bore 232 to receive the threaded end 46 of the femoral stem extension 18.

As can be seen in FIG. 4, the femoral component 12 is unchanged in this embodiment, which permits the same femoral component 12 to be used with femoral stems 16 that are adapted for either left or right femur usage. The concept of providing a common femoral component 12 that may be utilized in more than one application greatly increases the overall flexibility of the prosthesis of the present invention. FIG. 4 also shows a modified tibial component 118 in which the chamfer 120 on the tibial stem extension 90 has been moved to a more proximal location such that the chamfer 120 is located within the tibial stem 56. A chamfer 122 is provided in the bore 62 within the tibial stem 56 to mate with the chamfer 120 on the tibial stem extension 90. Relocating the chamfer 120 proximally into the tibial stem 56 increases the overall strength of the modified tibial portion 118 because the tibial stem extension maintains a somewhat greater diameter over a greater portion of its length.

FIG. 5 shows a stub stem extension 126 that may be utilized with the femoral portion 10 illustrated in FIG. 1 when the femoral stem extension 18 is not utilized. It will be understood that, depending upon the requirements of the individual patient, the femoral stem extension 18 may or may not be desirable. When the femoral stem extension 18 is not utilized, the stub stem extension 126 is inserted through the bore 38 in the femoral stem 16 to secure the femoral stem 16 to the femoral component 12. The stub stem extension 126 includes a threaded end 128 that engages the nut 32 to secure the femoral stem 16 to the femoral component 12.

FIG. 6 shows a modified tibial portion 136 with a tibial component 138 being a separate component from a tibial stem 140. It will be understood that providing a separate tibial component 138 and a separate tibial stem 140 increases the flexibility of the prosthesis. The tibial component 138 is generally formed like the tibial component 54 illustrated in FIG. 2, and includes a hole 142 that aligns with a bore 146 in the tibial stem 140. Two ribs 144 are formed on the lower, or distal side of the tibial component 138 that are adapted to extend into two depressions 148 formed on the upper, or proximal surface 150 of the tibial stem 140. The ribs 144 and depressions 148 cooperate to properly position the tibial component 138 with respect to the tibial stem 140, and also to prevent relative movement between the two components when assembled. The tibial stem 140, like the tibial stem 56, may have any of the surface treatments described previously. Illustratively, the tibial stem 140 is shown having a coated surface treatment.

FIG. 7 shows a modified tibial stem extension 154 in which a distal portion 156 is somewhat curved. It will be understood that it is sometimes desirable to use tibial stem extensions having different shapes to accommodate the anatomical requirements of an individual patient. Again, the distal portion 156 may have any of the surface treatments discussed previously. FIG. 7 shows the distal portion 156 having a coated surface treatment for illustrative purposes. The tibial stem extension 154 includes a proximal end 158 that is formed to include a threaded hole 160. The threaded hole 160 is provided to replace the threaded end 96 on the tibial stem extension 90 shown in FIG. 2. When the tibial stem extension 154 is utilized having a threaded hole 160, a bolt 164 as shown in FIG. 8 is provided that includes a threaded end 166 that is configured to mate with the threaded hole 160. It will be understood that the bolt 164 and threaded hole 160 cooperate in a manner identical to the nut 74 and the threaded end 96 of the tibial stem extension 90 illustrated in FIG. 2 to secure the components of the tibial portion together. It will be further understood that the tibial stem extension 154 having the curved distal portion 156 may be formed to alternatively include either the threaded hole 160 or a threaded end identical to threaded end 96 on the tibial stem extension 90 shown in FIG. 2.

FIGS. 9 and 10 illustrate the use of the tibial component 138 without any tibial stem being attached. It will be understood that, under certain circumstances, only the extreme proximal portion of the tibia need be replaced. In such a case, the tibial component 138 may be utilized separately. The ribs 144 on the tibial component 138 act as posts to extend into the tibia 112. Utilizing conventional procedures, the tibial component 138 can be secured to the tibia 112 using a grouting or bone cement material (not shown). The tibial insert 66 is shown in FIG. 9 to be secured to the tibial component 138 by the use of the bolt 164 in cooperation with a threaded stub 170. To increase the flexibility of the system, the tibial insert 66 can be secured to the tibial component 138 by using the nut 74 and a cooperating bolt 174 as illustrated in FIG. 10.

FIG. 11 shows a modified femoral portion 178 that includes a somewhat different structure for attaching a femoral component to a femoral stem. Specifically, FIG. 11 shows a femoral component 180 that includes two opposing, arcuate-shaped depressions 184. The arcuate-shaped depressions 184 are oriented and sized to receive ears 188 formed on a plate 186. It will be understood that the plate 186 is adapted to replace the nut 28 shown in FIG. 1. The plate 186 is formed to include a hole 190 that is sized to receive a screw 192. A modified femoral stem 194 is provided that includes a distal planar surface 196 for engaging the femoral component 180. The femoral stem 194 may have any of the surface treatments described previously, with a coated surface treatment illustrated.

To assemble the femoral portion 178, the distal surface 196 of the femoral stem 194 is engaged with the interior of the femoral component 180. The plate 186 is then engaged with the femoral component 180 such that the ears 188 extend into the arcuate-shaped depressions 184. The screw 192 is then inserted through the hole 190 and into a threaded hole 195 formed in the femoral stem 194. It will be understood that the femoral stem 194 can have any number of different shapes and sizes, with a somewhat square shape illustrated.

FIG. 12 shows a modified femoral stem extension 198 similar to the femoral stem extension 18 in FIG. 1. The modified femoral stem extension 198 includes a proximal curved portion 200 that may be desirable to accommodate different anatomical requirements of an individual patient. It will be understood that the femoral stem extension 198 is interchangeable with the femoral stem extension 18 in FIG. 1. The proximal curved portion 200 of the femoral stem extension 198 may have any of a surface treatments described previously, with a coated surface treatment illustrated.

Although specific embodiments of the present invention have been shown in FIGS. 1-12, it will be understood that the components shown in the figures may be interchangeable, and a knee prosthesis may be assembled utilizing combinations of the illustrated components. This ability to select different sizes and shapes of components to assemble a knee prosthesis greatly increases the flexibility available at the time of the operation. Thus, depending upon the anatomical indications presented by the patient, numerous combinations are available to assemble a knee prosthesis at the time of the operation to meet the exact requirements for that patient.

Although the invention has been described in detail with reference to preferred embodiments and specific examples, variations and modifications exist within the scope and spirit of the invention as described and defined in the following claims.

What is claimed is:

1. A modular knee prosthesis assembly for the replacement of an end portion of a leg bone contiguous to the knee joint, the assembly comprising:
    a first component having obverse and reverse surfaces and a central aperture connecting the two surfaces, the obverse surface being shaped to cooperate with a confronting portion of an adjacent bone or the like forming a knee joint, the obverse surface including a fastener-engaging portion adjacent the central aperture,
    a second component having an obverse surface engaging the reverse surface of the first component, an axial bore extending in line with the aperture of the first component, and a contact surface surrounding a reverse end of the axial bore,
    a third component having a surface contacting the contact surface of the second component and a coupling means for coupling the third component to a fastener component, and
    a fastener component inserted into the central aperture of the first component, engaged to the fastener-engaging portion of the first component, and coupled to the coupling means of the third component in direct mechanical interlock to secure the components in compressively assembled condition.

2. The modular knee prosthesis assembly of claim 1 wherein the obverse surface of the first component includes condyle surfaces adapted to contact a proximal portion of a tibia or the like, the condyle surfaces straddling said aperture.

3. A modular knee prosthesis assembly according to claim 1 wherein the third component includes a major portion protruding into said axial bore of the second component from the reverse end thereof, and said coupling means is situated on at least part of the portion of the third component protruding into the axial bore.

4. The modular knee prosthesis assembly of claim 1 wherein the obverse surface of the first component includes two slightly concave bearing surfaces adapted to support and mate with articulating surfaces of the distal end of a femur or the like.

5. The modular knee prosthesis assembly of claim 1 wherein the reverse surface of the first component includes two posts extending rearwardly on either side of the second component.

6. The modular knee prosthesis assembly of claim 1 wherein said fastener-engaging portion of the first component comprises an angled ledge and wherein the fastener component includes angled faces that made mate with the angled ledges to position and hold the fastener component relative to the first component.

7. A modular knee prosthesis assembly according to claim 1 wherein the fastener-engaging portion of the first component comprises a circumferential ledge contiguous to the central aperture and wherein the fastener component includes a shoulder cooperatively engaging the ledge.

8. The modular knee prosthesis assembly of claim 1 wherein the axial bore of the second component is inclined with respect to a line normal to the obverse surface of the second component.

9. The modular knee prosthesis assembly of claim 1 wherein the second component further comprises a rim circumscribing the obverse surface of the second component and the reverse surface of the first component.

10. A modular knee prosthesis assembly of claim 1 wherein the reverse surface of the first component includes a platform and the obverse surface of the second component includes a platform-engaging portion for restricting relative movement between the first and second components.

11. A modular knee prosthesis assembly for the replacement of an end portion of a leg bone contiguous to the knee joint, the assembly comprising:
    a first component having obverse and reverse surfaces and a central aperture connecting the two surfaces, the obverse surface being shaped to cooperate with a confronting portion of an adjacent bone or the like forming a knee joint, the obverse surface including a fastener-engaging portion adjacent the central aperture,
    a second component having an obverse surface engaging the reverse surface of the first component, an axial bore extending in line with the aperture of the first component, and a reverse surface including a pair of rearwardly extending protrusions straddling the axial bore of the second component,
    a third component having an obverse surface including a pair of depressions receiving the projections of the reverse surface of the second component, the third component having an axial bore extending in line with the aperture of the first component and axial bore of the second component, and
    fastener means inserted into the central aperture of the first component to engage the fastener engaging portion and coupled in the axial bore of the second component to secure the components in compressively assembled condition.

12. The modular knee prosthesis assembly of claim 11 wherein the fastener means comprises a plate including a central aperture and an edge configuration engaging the fastener-engaging portion of the first component, and a fastener inserted through the central aperture of the plate to couple the plate to the second component.

13. The apparatus of claim 11 wherein the obverse surface of the first component comprises condyle surfaces shaped to cooperate with a confronting portion of a tibia, the condyle surfaces straddling said central aperture.

14. The modular prosthesis of claim 11 further comprising a fourth component having a major portion protruding into said axial bore of the third component from the proximal end thereof and coupling means on a distal end for coupling to said fastener means.

* * * * *

UNITED STATES PATENT AND TRADEMARK OFFICE
CERTIFICATE OF CORRECTION

PATENT NO. : 4,822,366

DATED : April 18, 1989

INVENTOR(S) : Richard C. Bolesky

It is certified that error appears in the above-identified patent and that said Letters Patent is hereby corrected as shown below:

At column 2, line 65, please delete "with-out" and insert therefor --without--;

At column 5, line 31, after the word "stem", please insert --16--;

At column 5, line 56, please delete "this-.-embodiment." and insert therefor --this embodiment--; and At column 10, line 11, please delete "made".

Signed and Sealed this

Twenty-third Day of January, 1990

Attest:

JEFFREY M. SAMUELS

Attesting Officer     Acting Commissioner of Patents and Trademarks